US010285720B2

(12) United States Patent
Gilvarry et al.

(10) Patent No.: US 10,285,720 B2
(45) Date of Patent: May 14, 2019

(54) CLOT RETRIEVAL SYSTEM FOR REMOVING OCCLUSIVE CLOT FROM A BLOOD VESSEL

(71) Applicant: Neuravi Limited, Galway (IE)

(72) Inventors: Michael Gilvarry, County Galway (IE); David Vale, County Galway (IE); Brendan Casey, Galway (IE); Kevin McArdle, County Galway (IE); Jacqueline O'Gorman, County Clare (IE)

(73) Assignee: Neuravi Limited, Galway (IE)

( * ) Notice: Subject to any disclaimer, the term of this patent is extended or adjusted under 35 U.S.C. 154(b) by 519 days.

(21) Appl. No.: 14/644,685

(22) Filed: Mar. 11, 2015

(65) Prior Publication Data
US 2015/0257775 A1 Sep. 17, 2015

Related U.S. Application Data

(60) Provisional application No. 61/951,270, filed on Mar. 11, 2014.

(51) Int. Cl.
*A61B 17/221* (2006.01)
*A61F 2/01* (2006.01)
(Continued)

(52) U.S. Cl.
CPC .... *A61B 17/221* (2013.01); *A61B 2017/2212* (2013.01); *A61B 2217/005* (2013.01);
(Continued)

(58) Field of Classification Search
CPC . A61B 17/22; A61B 17/22031; A61B 17/221; A61B 2017/22034; A61B 2017/22035; A61B 2017/22072; A61B 2017/22094; A61B 2017/2212; A61B 2017/2215; A61B 2017/2217
See application file for complete search history.

(56) References Cited

U.S. PATENT DOCUMENTS 4,793,348 A 12/1988 Palmaz
4,873,978 A 10/1989 Ginburg
(Continued)

FOREIGN PATENT DOCUMENTS

DE 20 2009 001 951 U1 4/2010
DE 10 2009 056 450 A1 6/2011
(Continued)

OTHER PUBLICATIONS

US 6,348,062 B1, 02/2002, Hopkins (withdrawn)
(Continued)

*Primary Examiner* — Todd J Scherbel
(74) *Attorney, Agent, or Firm* — Troutman Sanders LLP

(57) ABSTRACT

A clot retrieval device comprising an elongate shaft having a proximal end and a distal end and a clot retrieval element at the distal end of the elongate shaft. A proximal end of the elongate shaft of the clot retrieval device is adapted for retraction of a first catheter over the clot retrieval device elongate shaft. A second catheter is advanced to or adjacent to the distal end of the clot retrieval device shaft to enable enhanced aspiration adjacent to the clot retrieval element.

19 Claims, 12 Drawing Sheets

(51) Int. Cl.
  *A61M 39/10*    (2006.01)
  *A61M 25/00*    (2006.01)
  *A61M 25/06*    (2006.01)
(52) U.S. Cl.
  CPC .............. *A61M 2025/0042* (2013.01); *A61M 2025/0681* (2013.01); *A61M 2039/1077* (2013.01)

(56) References Cited

U.S. PATENT DOCUMENTS

| | | |
|---|---|---|
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,171,233 A | 12/1992 | Amplatz |
| 5,234,437 A | 8/1993 | Sepetka |
| 5,387,219 A | 2/1995 | Rappe |
| 5,387,226 A | 2/1995 | Miraki |
| 5,449,372 A | 9/1995 | Schmaltz |
| 5,538,512 A | 7/1996 | Zenzon et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,695,519 A | 12/1997 | Summers et al. |
| 5,709,704 A | 1/1998 | Nott et al. |
| 5,713,853 A | 2/1998 | Clark |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Daniel et al. |
| 5,827,304 A | 10/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates |
| 6,350,271 B1 | 2/2002 | Kurz et al. |
| 6,361,545 B1 | 3/2002 | Macoviak et al. |
| 6,375,668 B1 | 4/2002 | Gifford et al. |
| 6,383,205 B1 | 5/2002 | Samson et al. |
| 6,383,206 B1 | 5/2002 | Gillick |
| 6,402,771 B1 | 6/2002 | Palmer |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,530,935 B2 | 3/2003 | Wensel |
| 6,530,939 B1 | 3/2003 | Hopkins |
| 6,540,768 B1 | 4/2003 | Diaz |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,175,655 B1 | 2/2007 | Malaei |
| 7,179,273 B1 | 2/2007 | Palmer et al. |
| 7,220,271 B2 | 5/2007 | Clubb |
| 7,226,464 B2 | 6/2007 | Garner et al. |
| 7,229,472 B2 | 6/2007 | DePalma et al. |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Clubb |
| 7,331,976 B2 | 2/2008 | McGuckin, Jr. et al. |

(56) References Cited

U.S. PATENT DOCUMENTS

| | | |
|---|---|---|
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne et al. |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Martin et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Imamura et al. |
| 2001/0001315 A1 | 5/2001 | Bates |
| 2001/0016755 A1 | 8/2001 | Addis |
| 2001/0051810 A1 | 12/2001 | Dubrul |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter et al. |
| 2002/0052620 A1 | 5/2002 | Barbut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0040772 A1 | 2/2003 | Hyodoh et al. |
| 2003/0050663 A1 | 3/2003 | Khachin |
| 2003/0125798 A1 | 7/2003 | Martin |
| 2003/0130682 A1 | 7/2003 | Broome et al. |
| 2003/0144687 A1 | 7/2003 | Brady et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0176884 A1 | 9/2003 | Berrada et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0236533 A1 | 12/2003 | Wilson |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153118 A1 | 8/2004 | Clubb |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |

(56) References Cited

U.S. PATENT DOCUMENTS

| | | |
|---|---|---|
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0125024 A1 | 6/2005 | Sepetka |
| 2005/0171566 A1 | 8/2005 | Kanamaru |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0267491 A1 | 12/2005 | Kellett et al. |
| 2005/0288686 A1 | 12/2005 | Sepetka |
| 2006/0009799 A1 | 1/2006 | Kleshinski et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1* | 9/2007 | Adams ............ A61B 17/12136 606/200 |
| 2007/0225749 A1 | 9/2007 | Martin |
| 2007/0244505 A1 | 10/2007 | Gilson et al. |
| 2007/0270902 A1 | 11/2007 | Slazas et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0312681 A1 | 12/2008 | Ansel |
| 2009/0024157 A1 | 1/2009 | Anukhin |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0292297 A1 | 11/2009 | Ferrere |
| 2009/0292307 A1 | 11/2009 | Razack |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnett et al. |
| 2010/0268265 A1 | 10/2010 | Krolik et al. |
| 2010/0318178 A1 | 12/2010 | Rapaport et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0054504 A1 | 5/2011 | Wolf et al. |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0276120 A1 | 11/2011 | Gilson et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0089216 A1 | 4/2012 | Rapaport et al. |
| 2012/0101510 A1 | 4/2012 | Lenker et al. |
| 2012/0143237 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0296362 A1 | 11/2012 | Cam et al. |
| 2012/0316600 A1 | 12/2012 | Ferrera et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1* | 8/2013 | Brady .................. A61B 17/221 606/200 |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0180377 A1 | 6/2014 | Bose et al. |
| 2014/0194919 A1 | 7/2014 | Losordo et al. |
| 2014/0200608 A1 | 7/2014 | Brady et al. |
| 2014/0236220 A1 | 8/2014 | Inoue |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |

(56) References Cited

U.S. PATENT DOCUMENTS

| | | |
|---|---|---|
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0112376 A1 | 4/2015 | Molaei et al. |
| 2015/0133990 A1 | 5/2015 | Davidson |
| 2015/0164523 A1 | 6/2015 | Brady et al. |
| 2015/0250497 A1 | 9/2015 | Marks et al. |
| 2015/0257775 A1 | 9/2015 | Gilvarry et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Seifert et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0317168 A1 | 11/2016 | Brady et al. |
| 2017/0071614 A1 | 3/2017 | Vale et al. |
| 2017/0086862 A1 | 3/2017 | Vale et al. |
| 2017/0086863 A1 | 3/2017 | Brady et al. |
| 2017/0105743 A1 | 4/2017 | Vale et al. |
| 2017/0112515 A1 | 4/2017 | Brady et al. |

FOREIGN PATENT DOCUMENTS

| | | |
|---|---|---|
| DE | 10 2010 010 849 A1 | 9/2011 |
| DE | 10 2010 014778 A1 | 10/2011 |
| DE | 10 2010 024 085 A1 | 12/2011 |
| DE | 10 2011 014 586 B3 | 9/2012 |
| EP | 2301450 B1 | 3/2011 |
| EP | 2628455 A1 | 8/2013 |
| JP | 0919438 A1 | 1/1997 |
| WO | WO 94/24926 | 11/1994 |
| WO | WO 97/27808 | 8/1997 |
| WO | WO 97/038631 A | 10/1997 |
| WO | WO 99/20335 | 4/1999 |
| WO | WO 99/60933 | 12/1999 |
| WO | WO 99/56801 | 4/2000 |
| WO | WO 01/21077 | 3/2001 |
| WO | WO 2004/056275 A1 | 7/2001 |
| WO | WO 02/02162 | 1/2002 |
| WO | WO 02/11627 | 2/2002 |
| WO | WO 02/43616 | 6/2002 |
| WO | WO 02/070061 | 9/2002 |
| WO | WO 02/094111 | 11/2002 |
| WO | WO 03/002006 | 1/2003 |
| WO | WO 03/030751 | 4/2003 |
| WO | WO 03/051448 | 6/2003 |
| WO | WO 2004/028571 A2 | 4/2004 |
| WO | WO 2005/000130 A1 | 1/2005 |
| WO | WO 2005/027779 A2 | 3/2005 |
| WO | WO 2006/021407 | 3/2006 |
| WO | WO 2006/031410 | 3/2006 |
| WO | WO 2006/107641 | 10/2006 |
| WO | WO 2006/135823 A2 | 12/2006 |
| WO | WO 2007/054307 | 5/2007 |
| WO | WO 2007/068424 | 6/2007 |
| WO | WO 2008/034615 | 3/2008 |
| WO | WO 2008/051431 A1 | 5/2008 |
| WO | WO 2008/131116 | 10/2008 |
| WO | WO 2009/031338 A1 | 3/2009 |
| WO | WO 2009/076482 | 6/2009 |
| WO | WO 2009/086482 | 7/2009 |
| WO | WO 2009/105710 A1 | 8/2009 |
| WO | WO 2010/010545 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A9 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/134625 A1 | 9/2015 |
| WO | WO 2015/179324 A2 | 11/2015 |
| WO | WO 2015/189354 A1 | 12/2015 |
| WO | WO 2016/010995 A1 | 1/2016 |

OTHER PUBLICATIONS

International Search Report of PCT/IE2012/000011, dated Oct. 10, 2012 (3 pages).

Written Opinion and International Search Report, dated Jul. 27, 2011, from international Application No. PCT/IE2011/000026 (8 pages).

International Search Report of PCT/IE2011/000057, dated Feb. 3, 2012 (5 pages).

* cited by examiner

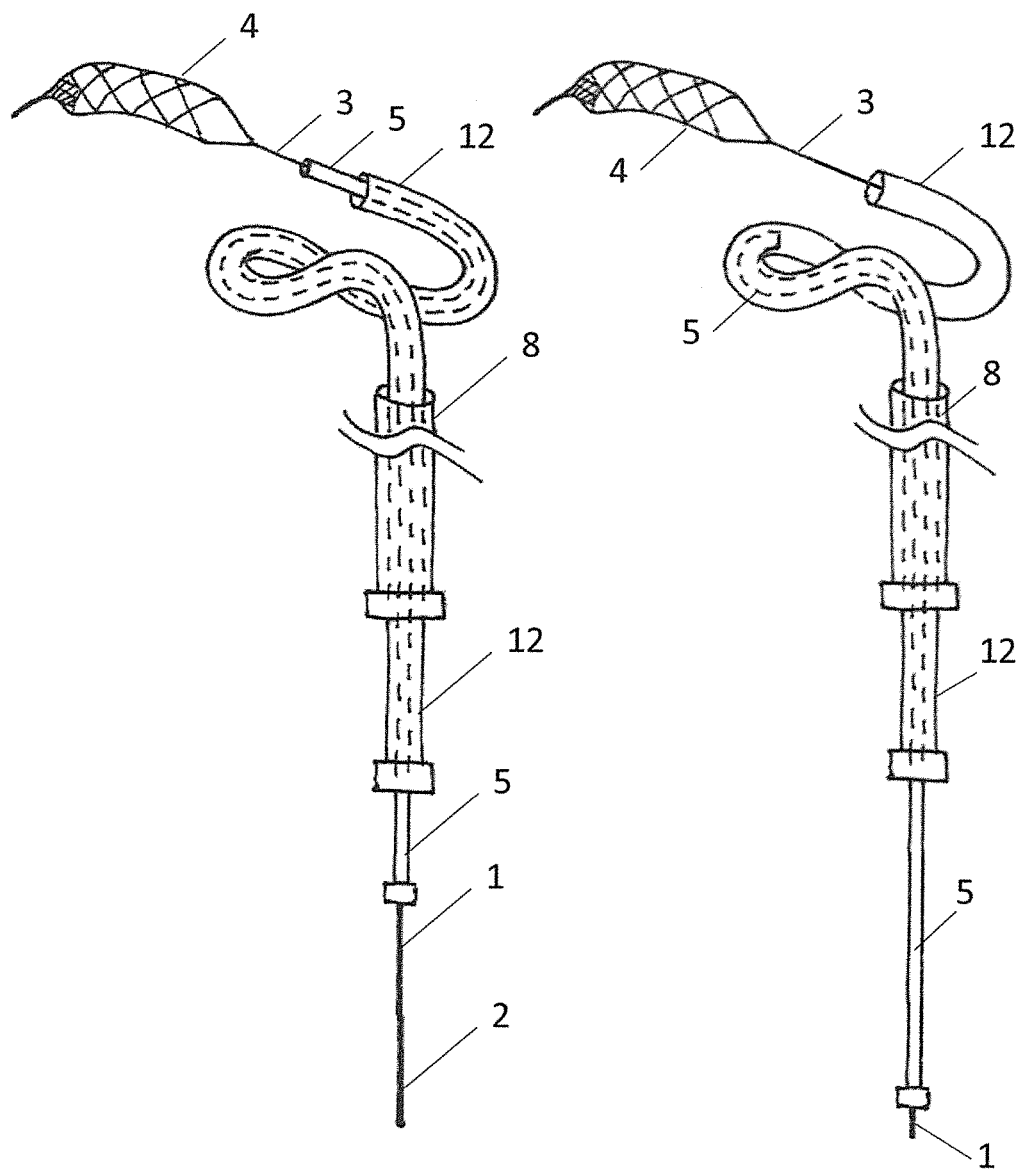

Prior Art

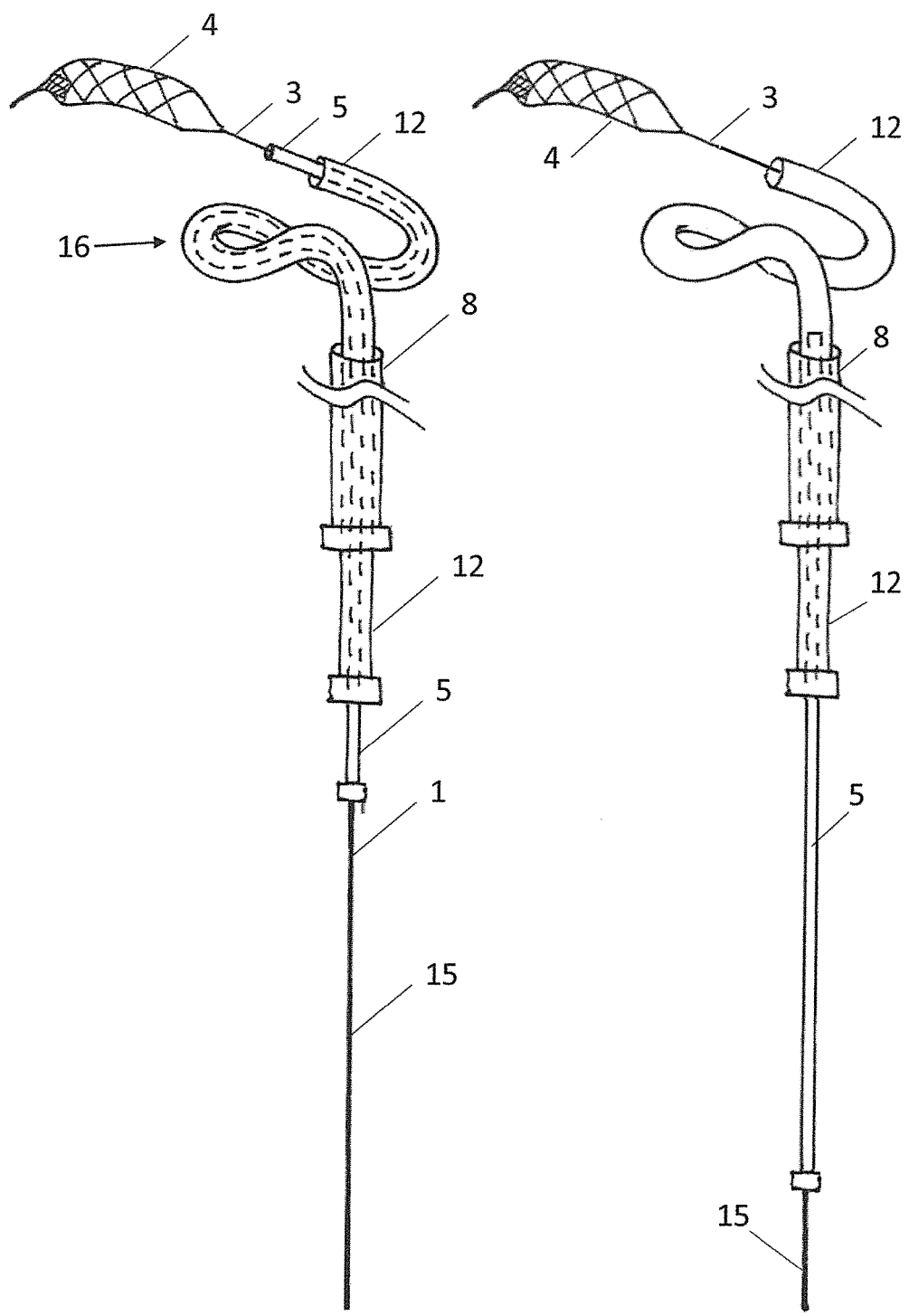

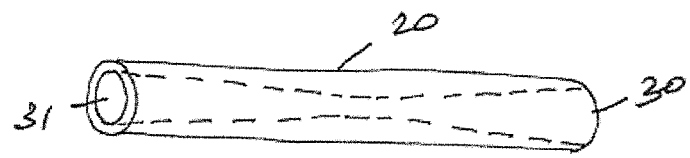
Fig 14
Fig 15
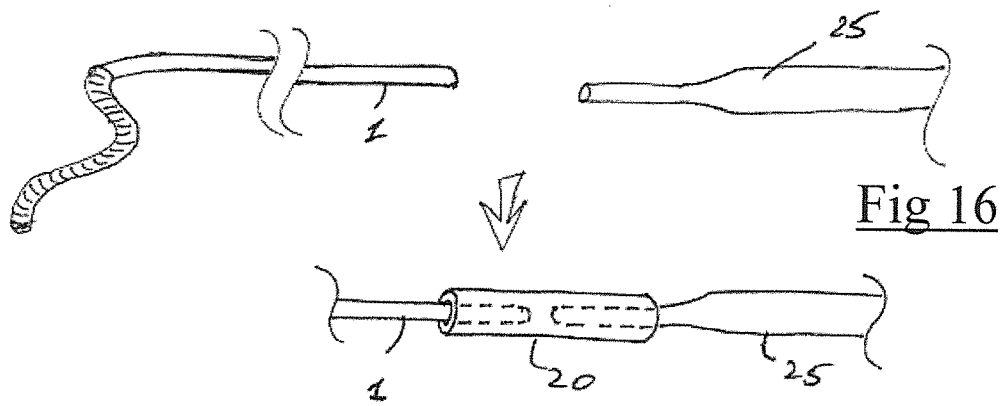
Fig 16
Fig 17

CLOT RETRIEVAL SYSTEM FOR REMOVING OCCLUSIVE CLOT FROM A BLOOD VESSEL

CROSS REFERENCE TO RELATED APPLICATIONS

This application claims the benefit of U.S. Provisional Application No. 61/951,270, filed Mar. 11, 2014, the disclosure of which is incorporated herein by reference in its entirety.

FIELD OF THE INVENTION

This invention relates to devices and methods of removing acute blockages from blood vessels. The invention especially relates to removing acute obstructions from blood vessels. Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages and can also occur in the cerebral vasculature.

BACKGROUND

There are significant challenges associated with designing clot removal systems that can deliver high levels of performance:

There are a number of access challenges that make it difficult to deliver devices. In cases where access involves navigating the aortic arch (such as coronary or cerebral blockages) the configuration of the arch in some patients makes it difficult to position a guide catheter. These difficult arch configurations are classified as either type 2 or type 3 aortic arches with type 3 arches presenting the most difficulty. The tortuosity challenge is even more severe in the arteries approaching the brain. For example it is not unusual at the distal end of the internal carotid artery that the device will have to navigate a vessel segment with a 180° bend, a 90° bend and a 360° bend in quick succession over a few centimeters of vessel. In the case of pulmonary embolisms, access may be gained through the venous system and then through the right atrium and ventricle of the heart. The right ventricular outflow tract and pulmonary arteries are delicate vessels that can easily be damaged by inflexible or high profile devices. For these reasons it is desirable that the clot retrieval device be compatible with as low profile and flexible access and support catheters as possible.

The vasculature in the area in which the clot may be lodged is often fragile and delicate. For example neurovascular vessels are more fragile than similarly sized vessels in other parts of the body and are in a soft tissue bed. Excessive tensile forces applied on these vessels could result in perforations and haemorrhage. Pulmonary vessels are larger than those of the cerebral vasculature, but are also delicate in nature, particularly those more distal vessels.

The clot may comprise any of a range of morphologies and consistencies. Long strands of softer clot material may tend to lodge at bifurcations or trifurcations, resulting in multiple vessels being simultaneously occluded over significant lengths. More mature and organized clot material is likely to be less compressible than softer fresher clot, and under the action of blood pressure it may distend the compliant vessel in which it is lodged. Furthermore the inventors have discovered that the properties of the clot may be significantly changed by the action of the devices interacting with it. In particular compression of blood clot causes dehydration of the clot and results in a dramatic increase in both clot stiffness and coefficient of friction.

The clots may not only range in shape and consistency, but also may vary greatly in length, even in any one given area of the anatomy. For example clots occluding the middle cerebral artery of an ischemic stroke patient may range from just a few millimeters to several centimeters in length.

In the case of an intracranial occlusion a variety of access routes are possible with known devices, including a direct stick into the carotid artery, a brachial approach, or a femoral access. Once access has been gained to the arterial system using conventional and well understood techniques, a guide catheter or long sheath is typically placed as close to the occlusive clot as practical. For example, In the case of a middle cerebral artery occlusion the guide catheter might be placed in the internal carotid artery proximal of the carotid siphon. A microcatheter is then advanced across clot, typically with the aid of a guidewire. In some cases an additional catheter (which may be known as a Distal Access Catheter or DAC) may be used in a triaxial system such that the microcatheter is advanced through the DAC, which is in turn advanced through the guide catheter or long sheath. Once the microcatheter tip has been advanced across and distal of the clot the guidewire is removed and the clot retrieval device is advanced through the microcatheter until it reaches its distal end. The microcatheter is then retracted, allowing the clot retrieval device to expand within and on either side of the clot.

A particular problem arises with known systems because of the multiple catheters/shafts required to be in place at various stages during the procedure. For example in many cases it is desirable to be able to aspirate (apply a suction force) through the guide/sheath or DAC to assist in the withdrawal of the clot. The effectiveness of this aspiration can be hindered by the presence of catheter shafts within the aspiration lumen, and it is therefore sometimes desirable to be able to remove the microcatheter prior to aspiration and clot retrieval. The vessels through which the catheters are passed are very narrow and in most cases very tortuous. Thus, the anatomy presents major challenges to removing or advancing further devices or catheters that may be required during a procedure, as clot retrieval device shafts are typically not exchange length.

In general, there is a need to provide a clot retrieval system which provides the required flexibility to a physician to deal with a wide range of clots, often in an emergency situation.

STATEMENT OF THE INVENTION

According to the invention there is provided a clot retrieval device comprising an elongate shaft having a proximal end and a distal end; and a clot retrieval element at the distal end of the elongate shaft, a proximal end of the elongate shaft of the clot retrieval device being adapted for retraction of a first catheter over said clot retrieval device elongate shaft, a second catheter being advanced to or adjacent to the distal end of the clot retrieval device shaft to enable enhanced aspiration adjacent to the clot retrieval element.

In one embodiment aspiration is delivered through the second catheter, the lumen of the second catheter being larger than the lumen of the first catheter. The first catheter may comprise a microcatheter through which the clot retrieval device is delivered. In one case the second catheter an intermediate catheter.

In one case the proximal end of the shaft is adapted for retraction of a first catheter having a lumen and subsequent advancement of a second catheter having a lumen. In one case the lumen of the second catheter being larger than the lumen of the first catheter.

In one case the proximal end of the shaft is adapted for retraction and removal of a first catheter having a lumen through the second catheter.

In one embodiment the device comprises an adaptor at the proximal end of the elongate shaft, the adaptor being adapted to receive a shaft extension section.

The adaptor may be integral with the shaft proximal section. For example, the adaptor may comprise a receiver which is adapted to receive a shaft extension section.

In another embodiment the adaptor is releasably mountable to the proximal end of the elongate shaft. The adaptor may comprise a mounting section for mounting to the proximal end of the shaft and a receiver which is adapted to receive a shaft extension section. In some cases, the adaptor mounting section is a push fit with the proximal end of the shaft. The adaptor receiver may be a push fit with a shaft extension.

The invention also provides a clot retrieval device of the invention and an adaptor for mounting to a proximal end of the elongate shaft of the clot retrieval device. The adaptor may comprise a mounting section for mounting to the proximal end of the shaft and a receiver which is adapted to receive a shaft extension section. The adaptor mounting section may be a push fit with the proximal end of the shaft. The adaptor receiver may be a push fit with a shaft extension.

In one embodiment the adaptor is configured to accept the proximal end of a standard guidewire. Thus, the guide wire that was initially used to aid advancement of the microcatheter can be used or re-used as a shaft extender.

In one case the clot retrieval device shaft has at least one tactile feature at/or adjacent to the proximal end thereof.

In one embodiment the clot retrieval device shaft has at least one high friction feature at/or adjacent to the proximal end thereof.

Also provided is a clot retrieval device wherein the shaft of the clot retrieval device is extendable. This concept could be applied to any endovascular medical device in which the extension of the device shaft is advantageous.

The proximal region of the device shaft may be tubular and a shaft extension member is movable from a retrieval configuration in which the extension member is within the proximal region to an extended configuration in which the extension member is at least partially extended proximally from the proximal region of the device shaft.

In one case the tubular proximal region and/or the extension member comprises at least one stop to set the length to which the extension member may extend from the tubular proximal region and/or to control the degree of push that may be applied to the extension member.

The invention also provides method for retrieving a clot from a vasculature comprising the steps of providing a clot retrieval device having a compressed or retracted delivery configuration and an expanded deployed configuration, the clot retrieval device having an elongate shaft; providing a first catheter; providing a second catheter; deploying the clot retrieval device at/or adjacent to the clot; and retracting the first catheter over the clot retrieval device shaft whilst maintaining control of the proximal end of the retrieval device shaft.

The method may comprise applying aspiration to the clot through the lumen of the second catheter after retraction of the first catheter over the retrieval device shaft.

In one case the first catheter is a delivery catheter for the clot retrieval device and the method comprises deploying the retrieval device from the delivery catheter and subsequently retracting the delivery catheter over the clot retrieval device shaft.

The method may comprise the step of extending the length of the retrieval device shaft prior to retraction of the first catheter.

In one case the method comprises the steps of connecting one end of an adaptor to the proximal end of the device shaft and connecting as proximal shaft extension to the other end of the adaptor. In one case the device shaft comprises an extension member and the method compresses the steps of moving the extension member from a retracted to an extended configuration prior to retraction of the first catheter.

The method may comprise the step of extending the length of the clot retrieval device shaft and delivering the second catheter over the extended length of the device shaft and distally towards the clot.

BRIEF DESCRIPTION OF THE DRAWINGS

The invention will be more clearly understood from the following description of an embodiment thereof, given by way of example only, with reference to the accompanying drawings, in which:

FIGS. 2 and 3 are views of parts of the prior art clot retrieval system;

FIGS. 6 and 7 are views of a clot retrieval system according to the invention;

FIGS. 14 and 15 are views of further adaptors used in the invention;

FIGS. 16 and 17 are views of parts of the clot retrieval system and adaptors, in use;

DETAILED DESCRIPTION

Figure 1:
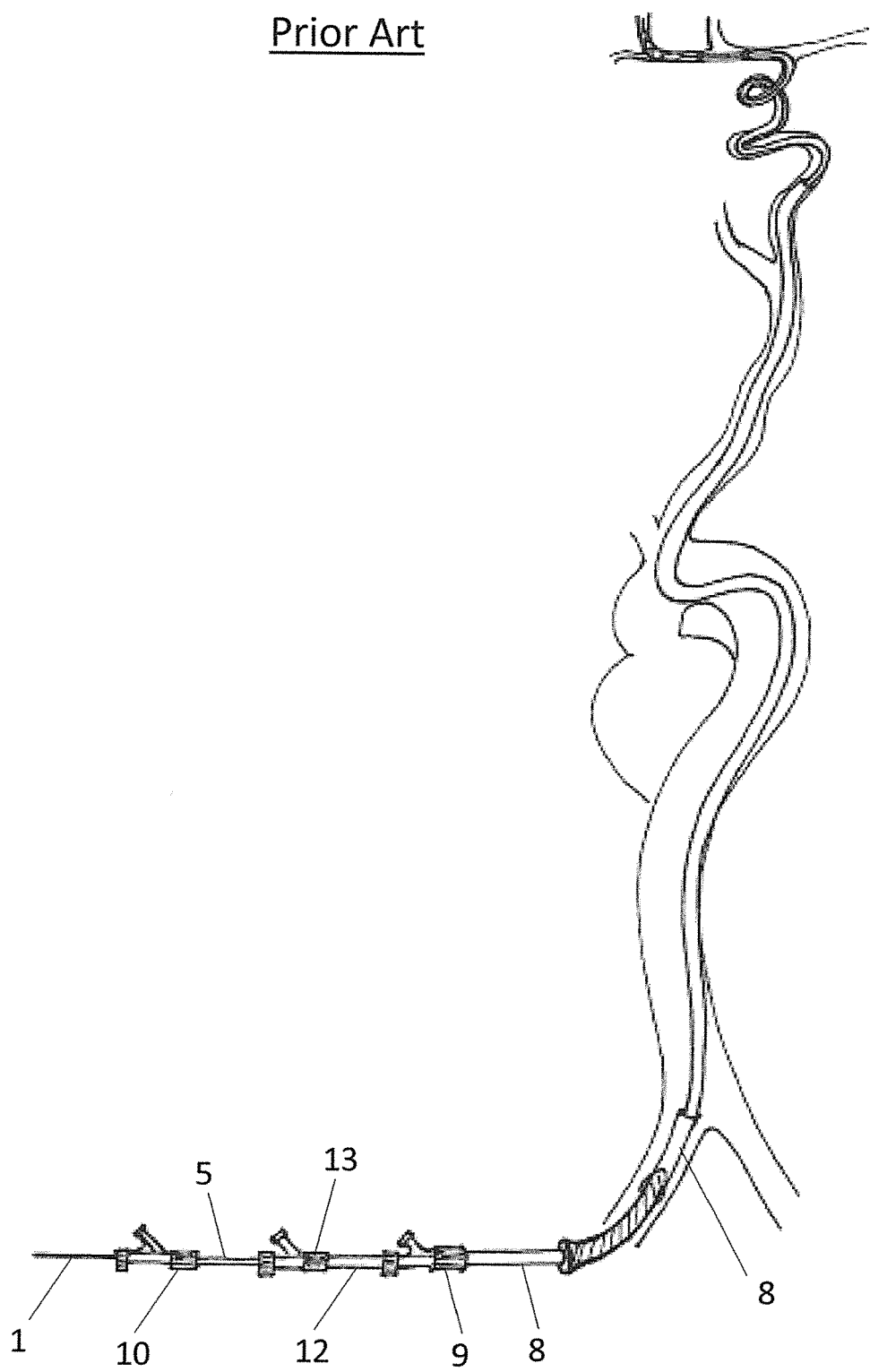
FIG. 1 is a diagram of a prior art clot retrieval system, in use.
Figure 4:
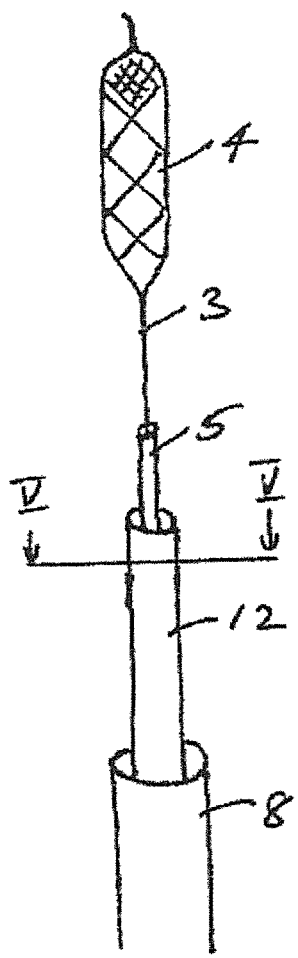
FIG. 4 is a view of a distal end of the prior art clot retrieval system.

Various devices and methods for removal of acute blockages from blood vessels are known. For example, various clot retrieval devices and methods of use are described in our WO2012/120490A and US2013-0345739A. The entire contents of all of the above-listed applications are herein incorporated by reference.

Known devices (FIGS. 1 to 5) generally comprise an elongate shaft 1 having a proximal end 2 and a distal end 3. A clot retrieval element 4 is mounted at the distal end of the elongate shaft. The clot retrieval element 4 may have a collapsed delivery configuration and an expanded deployed configuration. A microcatheter 5 is advanced across a clot with the aid of a guidewire. Once the microcatheter distal tip has been advanced across and distal of the clot the guide wire is removed and the clot retrieval element 4 and associated elongate shaft 1 is advanced through the microcatheter 5 in the collapsed delivery configuration. When the retrieval element 4 has crossed the clot through the microcatheter 5, the microcatheter 5 is then retracted, allowing the clot retrieval element 4 to expand within and on either side of the clot. In some cases a guide catheter 8 is first placed as close as possible to the occlusive clot as practical. The guide catheter 8 has a proximal connector 9 through which the microcatheter 5 is introduced. The microcatheter 5 has a proximal connector 10 through which the clot retrieval device is introduced through a connector 11. In some cases an additional catheter 12 with a proximal connector 13 (which may be known as a Distal Access Catheter or DAC) may be used in a triaxial system as illustrated in FIGS. 1 to 5. In this case the microcatheter 5 is introduced through the DAC 12 which in turn is advanced through the guide catheter 8.

Figure 5:
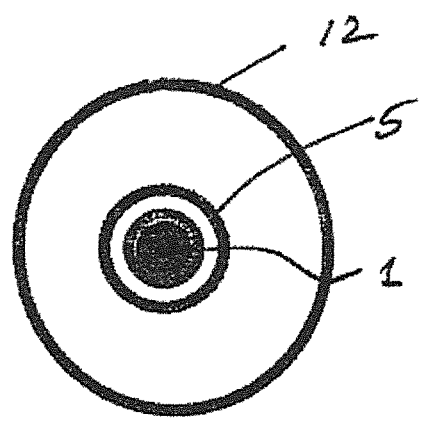
FIG. 5 is a cross sectional view on the line V-V in FIG. 4.
Figures 8, 9:
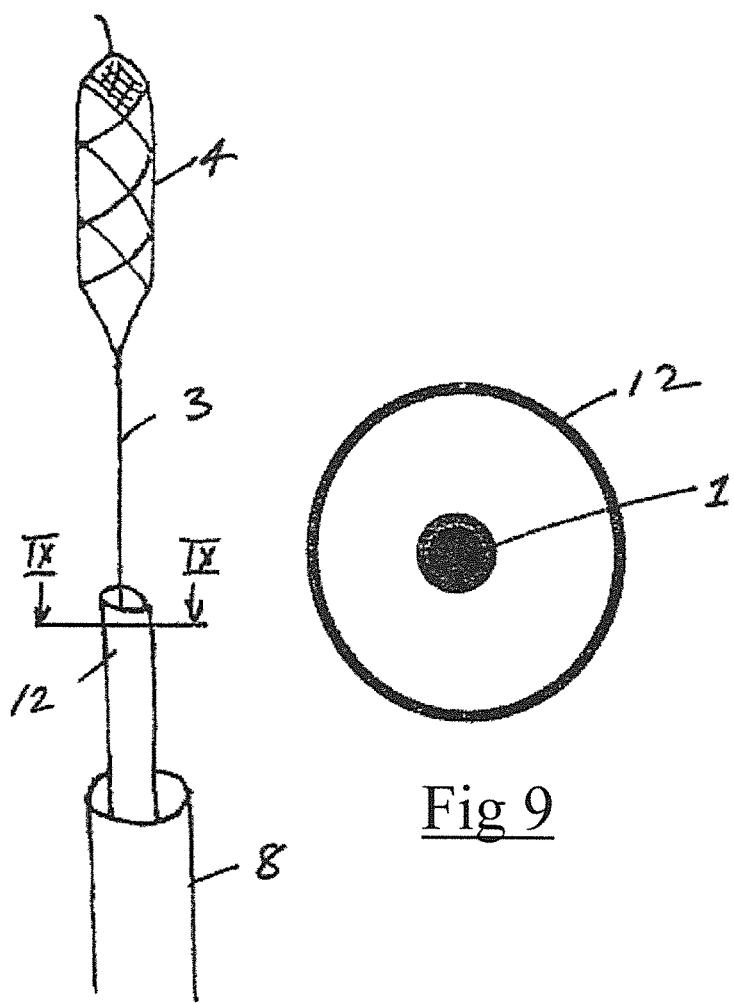
FIG. 8 is a view of a distal end of the clot retrieval system of FIGS. 6 and 7.
FIG. 9 is a cross sectional view on the line IX-IX in FIG. 8.
Figure 10:
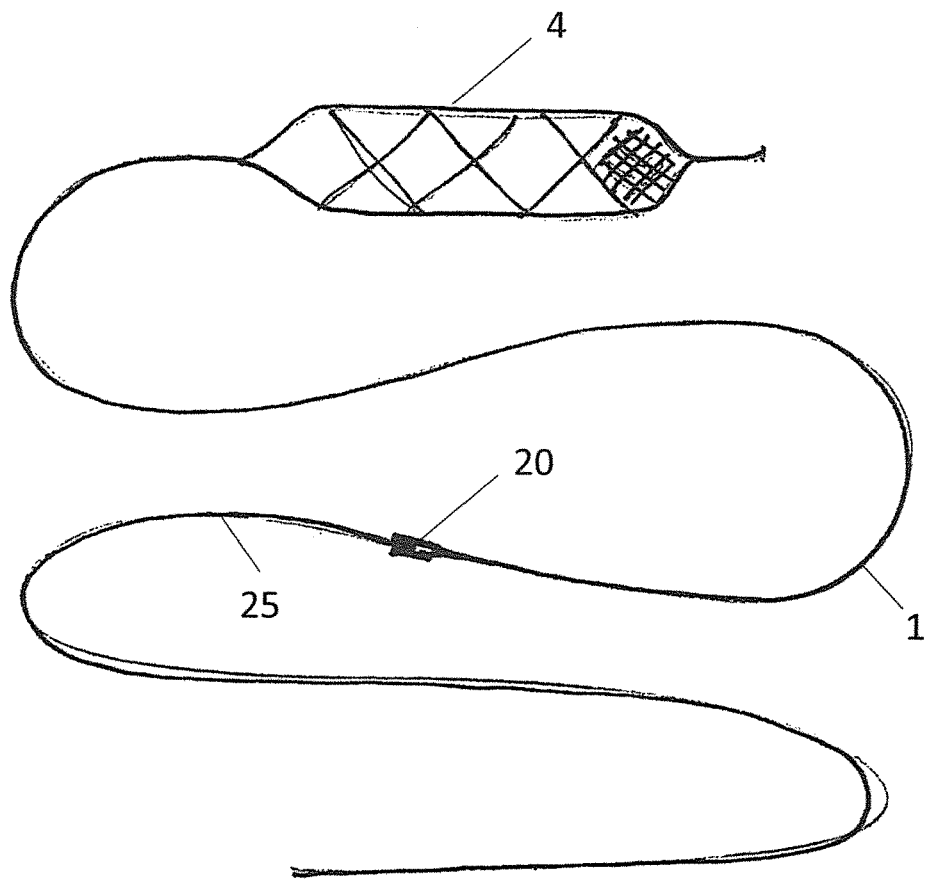
FIG. 10 is another view of a clot retrieval system of the invention including an adaptor.
Figure 11:
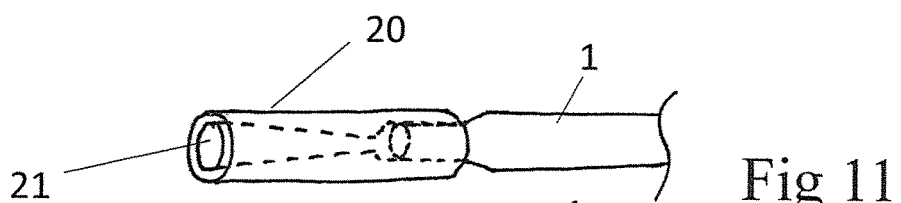
FIGS. 11 to 13 are view of various adaptors used in the invention.
Figure 12:
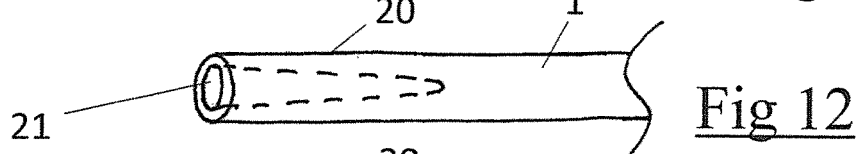
Figure 13:
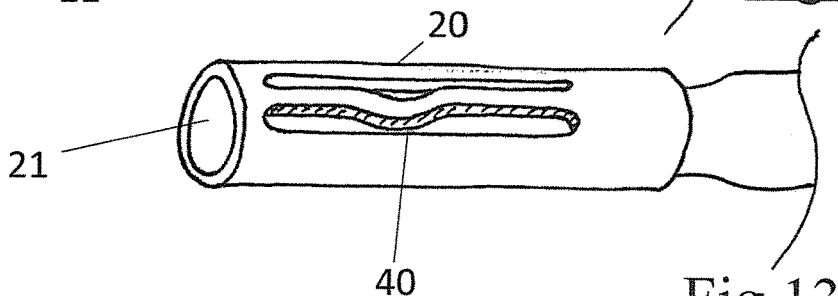

As explained above, there is a very wide variation in clot type, location and size, all of which influence the optimum procedural steps required for clot retrieval. In order to provide the clinician with the flexibility to cope with all eventualities, in the invention the proximal end 2 of the elongate shaft 1 of the retrieval device is adapted so that a first catheter such as the microcatheter 5 can be retracted over the shaft 1 and removed whilst still retaining control over the clot retrieval element from the proximal end of the shaft 1 of the retrieval device. This is important in facilitating further procedures initiated as close as possible to the clot through the maximum possible lumen size. The difference in lumen size will be particularly apparent by comparing FIG. 5 (prior art) and FIG. 9. FIGS. 5 and 9 are section view through FIGS. 4 and 8 respectively. In FIG. 9 the microcatheter is not obstructing the lumen of the additional catheter such as a DAC 12 so that the maximum lumen is available for example for aspiration and/or clot retrieval. For example, for a large clot or a clot which is difficult to dislodge, the second catheter may facilitate aspiration of the clot. Alternatively or additionally, the second catheter may facilitate more close control over a dislodged clot so that it is contained within the second catheter as close as possible to the original clot location. This minimises the risk of clot fragments becoming mobile in a section of the vasculature proximal to the clot location.

It will be appreciated that in prior art systems it is not possible to remove the microcatheter whilst still retaining control over the clot retrieval element 4 via the retrieval device shaft 1—pulling the microcatheter 5 proximally will occlude the shaft 1 at the proximal end 2. This presents a problem to the physician as he needs to let go of and lose control of the clot retrieval device shaft in order to fully remove the microcatheter. This could result in the clot retrieval element moving proximally, which could result in loss of captured clot. One solution to this would be to provide a very long clot retrieval device shaft, but such shaft would need to be greater than 3.5 meters in length in order to ensure that the shaft never becomes occluded by the microcatheter. Such a long shaft would be extremely cumbersome and would hinder the physician in cases where microcatheter removal was not required.

The inventors have discovered an adaption of the shaft length of the clot retrieval device that can be employed which allows safe microcatheter removal without adding a cumbersome length to the shaft 1. This shaft configuration is illustrated in FIGS. 6 and 7, and provides an additional length 15 to the proximal end of the clot retrieval device shaft 1 which corresponds to the length of significant vascular tortuosity 16 proximal to the clot retrieval element 4. This additional length 15 allows the user to retain control of the clot retrieval device shaft 1 while retracting the microcatheter 5 through this distal tortuosity. Once the microcatheter tip is proximal of this tortuosity the frictional force between the clot retrieval device shaft 1 and the microcatheter 5 drops significantly. In the case of femoral access to the cerebral vasculature a microcatheter of approximately 1.5 m is typically employed, and the clot retrieval device shaft is typically approximately 1.9 m. This 1.9 m shaft length is required in order that the microcatheter 5 can be retracted a few cm proximal of the clot retrieval device to deploy the device, while still leaving exposed clot retrieval device shaft 1 proximal of the proximal end of the microcatheter, which is typically fitted with a rotating haemostasis valve of approximately 7 cm in length. Extending this shaft 1 to at least 2.1 m, but ideally not more than 2.3 m will allow for the microcatheter to be retracted from the relatively tortuous vessels distal of the aortic arch without loss of the shaft access (as illustrated in FIG. 7), and without excessive shaft length protruding off the end of the hospital trolley bed on which the patient is lying.

An alternative means of retaining shaft control while removing a microcatheter is to provide a shaft extension. Such an extension could be a dedicated extension supplied for that very purpose, or could (preferably) be an alternative use of a standard guidewire, such as the guidewire that was used to advance the microcatheter into position in the first place. Enabling a standard guidewire to be used for this purpose is particularly advantageous for emergency acute stroke clot retrieval cases, because speed of recanalisation is such a vital factor to good patient outcomes. If the physician can save even a few seconds in restoring flow to the brain this can have a significant impact on the end result for the patient. Also these procedures are unplanned and after happen late at night or in the early morning, when only a small team are on call and finding accessory devices or extension wire is not as easy as it might be with a full team in the day time.

One embodiment of such an extension would be approximately the length of the microcatheter, so that the user could retain full control of the clot retrieval device shaft during microcatheter removal. Another embodiment of such an extension would be much shorter—less than 60 cm in length, or even as short as 15 cm or 20 cm in length, so that the user can could retain full control of the clot retrieval device shaft during the retraction of the microcatheter through the region of maximum distal tortuosity, but then release the shaft for full removal of the microcatheter from the patient.

Referring for example to FIGS. 10 to 13 in one case an adaptor 20 is provided which has a receiver 21 which is adapted to receive a shaft extension 25.

In some cases (for example FIG. 12) the adaptor 20 is integral with the proximal end of the shaft. In other cases (FIGS. 11, 13) the adaptor 20 may be releasably mountable to the proximal end of the shaft.

Referring to FIGS. 14 to 17 in this case an adaptor 20 has a mounting section 30 for mounting to the proximal end of the retrieval device shaft and a receiver 31 which is adapted to receive the shaft extension 25. Various designs are possible. The adaptor may be used to join the proximal end of the retrieval device shaft to a guidewire by a simple push fit (FIGS. 14 to 17). A mid to high modulus polymeric material with a high coefficient of friction may be used to provide a good interference fit. Alternatively (FIGS. 11 to 13) the adaptor may be of a metal such as nitinol or stainless steel or similar. In this case the adaptor may have an engagement feature 40 such as a taper and/or a clip or spring feature to positively engage with the proximal end of the retrieval device shaft and/or the extension shaft 25.

Figure 18:
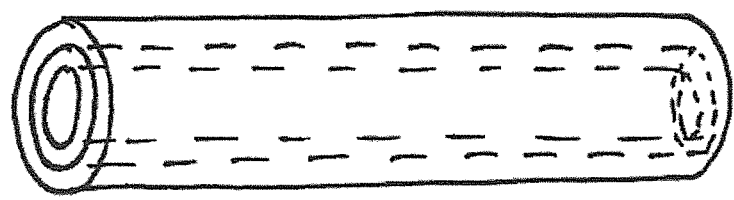
FIGS. 18 and 19 are views of further adaptors of the invention.
Figure 19:
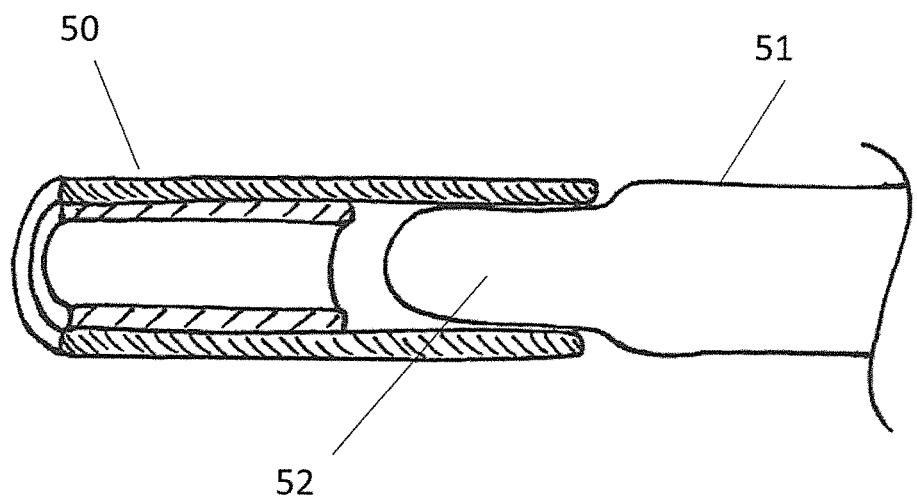
Figure 20:
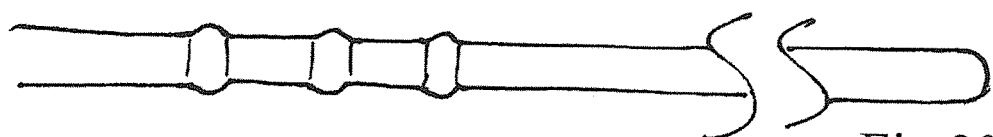
FIGS. 20 to 24 are views of a proximal section of a clot retrieval shaft with various proximal tactile features.
Figure 21:
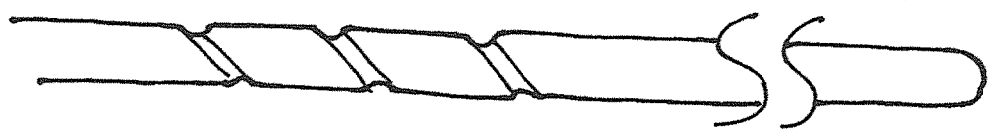
Figure 22:
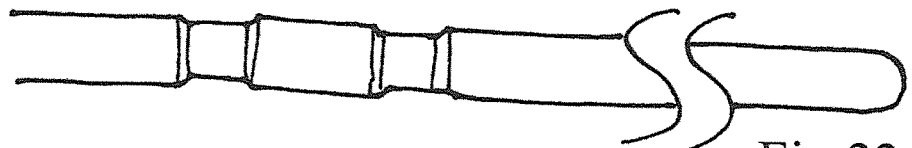
Figure 23:
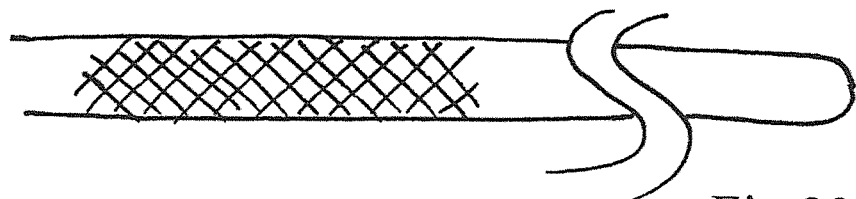
Figure 24:
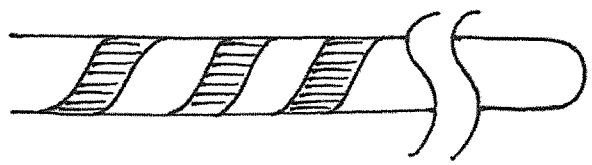

Referring to FIGS. 18 to 19 there is illustrated an adaptor 50 which in this case is configured to accept the proximal end 52 of a standard guide wire 51. In this case a guide wire 51 which was initially used to aid advancement of a microcatheter can now be used or re-used as a shaft extender.

Referring to FIGS. 20 to 24 in some embodiments tactile features such as bumps, grooves or surface indentations, raised areas or higher friction areas may be provided towards the proximal end of the elongate retrieval device shaft. These features can be used to provide two distinct benefits: 1) they can provide tactile feedback to the user to indicate when the clot retrieval element is approaching the distal end of the microcatheter. This means that the physician can advance the device quickly through the microcatheter without any need for x-ray guidance (minimising exposure to both patient and medical team) until he feels these tactile features. He can then slow down and advance the device carefully over the last few centimeters using x-ray/fluoroscopic guidance. 2) they can be used to provide a higher friction, easier to grip area of shaft to help the physician to advance the device through the more tortuous vasculature that typically exists adjacent the clot. This is particularly helpful when there is significant tortuosity to be navigated, because in these cases a higher force must be exerted to advance the device shaft. It is important that the section of shaft that is passing through tortuosity has a low coefficient of friction, so these higher friction "grip" features are ideally positioned only on a proximal region of the shaft.

Where the above mentioned tactile features are used to provide an indication to the user as to the position of the clot retrieval element relative to the end of the microcatheter they may be provided over a distance of 3 to 10 cm, possibly about 5 cm at a location which is a fixed distance from the distal end of the device, where said fixed distance is slightly less than the length of the microcatheter and adapter (typically a rotating haemostasis valve). For typical neurovascular microcatheters a distance of between 1.5 m and 1.65 m is suitable.

Figure 25:
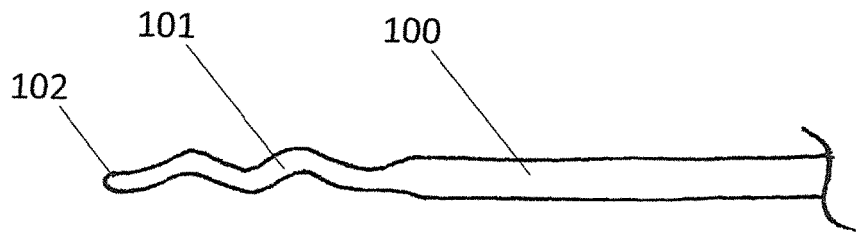
FIGS. 25 to 27 are views of proximal sections of clot retrieval shafts.
Figure 26:
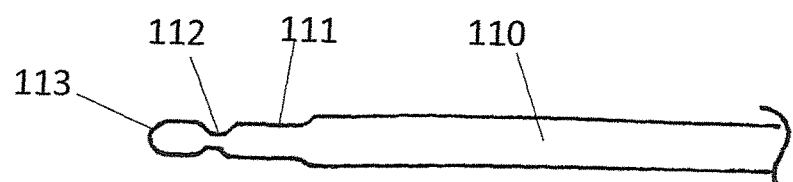
Figure 27:
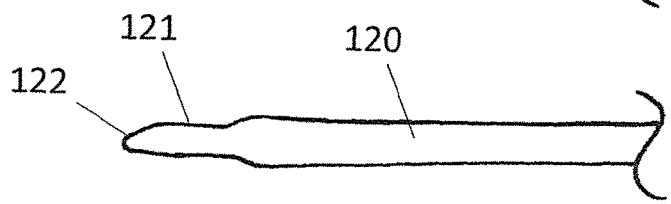

Referring to FIGS. 25 to 27 there are illustrated three examples of profiles of the proximal end of the shaft of a clot retrieval device which are configured to mate with a receiving portion or adaptor at the end of a shaft extension member.

FIG. 25 shows the proximal region of shaft 100 which comprises an undulating section 100 terminating in proximal end 102. Undulating section 101 is designed to create an interference fit in an adaptor such as that shown in FIG. 28, where the inner diameter 133 of adaptor 132 is smaller than the effective diameter of undulating section 101. Shaft 100 is preferably made from a relatively high modulus material such as stainless steel or Nitinol or other metal or alloy to provide the user with the means to transfer a push force through the shaft to its distal end. Shaft 100 may have an outer diameter of between 0.010" and 0.030", but preferably between 0.014" and 0.020" and most preferably between 0.016" and 0.018".

FIG. 26 shows the proximal region of shaft 110 which comprises a stepped proximal end with a reduced diameter section 111, a groove or channel 112 and a rounded proximal end 113. This shaft is configured to mate with adaptors of this invention such as the adaptor 142 shown in FIG. 29, such that the indented spring arm 143 aligns with the recessed channel 112, creating a type of snap-fit joint that can be attached or detached using a simple push or pull action.

FIG. 27 shows the proximal region of shaft 120 which comprises a reduced diameter section 121 and a tapered proximal end 122. This shaft is configured to mate with many of the previously disclosed adaptors of this invention and adaptors such as the adaptor 152 shown in FIG. 30.

Figure 28:
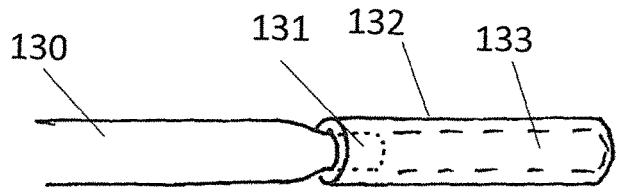
FIGS. 28 to 30 are views of various shaft extensions and adaptors of the invention.
Figure 29:
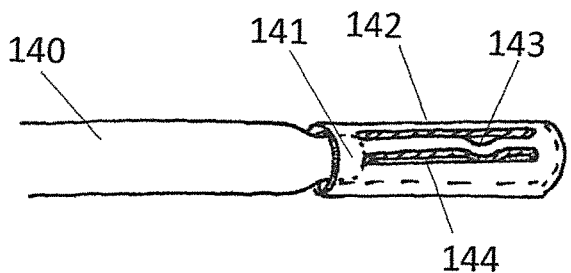
Figure 30:
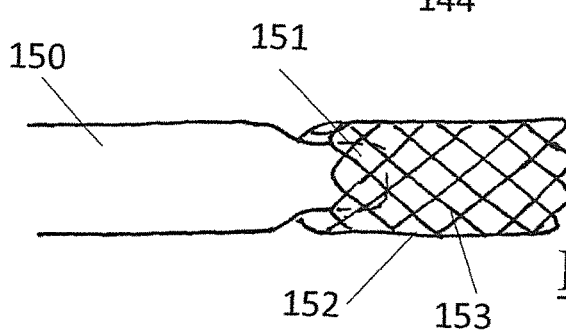

Referring to FIGS. 28 to 30 there are illustrated the distal portions of three examples of shaft extensions of this inventions incorporating adaptors configured to enable the extension to be attached to the proximal end of the shaft of a clot retrieval device.

FIG. 28 illustrates the distal portion of shaft extension 130, to which is attached adaptor 132. The distal end 131 of the shaft extension 130 is stepped down in diameter to fit within the lumen of adaptor 132 to which it is attached. This attachment may comprise a weld, a bond, an interference fit or other suitable attachment means. In one embodiment the extension and adaptor are made from a single piece of material (a monolithic structure). Adaptor 132 comprises a receiver 133 configured to mate with the proximal end of a shaft such as that shown in FIG. 25, or any such shaft with which it can create an interference fit. The shaft extension 130 is preferably made from a relatively high modulus material such as stainless steel or Nitinol or other metal or alloy. Adaptor 132 is preferably made from a similar family of materials.

FIG. 29 illustrates the distal portion of shaft extension 140, to which is attached adaptor 142. The distal end 141 of the shaft extension 140 is stepped down in diameter to fit within the lumen of adaptor 142 to which it is attached. This attachment may comprise a weld, a bond, an interference fit or other suitable attachment means. In one embodiment the extension and adaptor are made from a single piece of material (a monolithic structure). Adaptor 142 comprises an indented spring arm 143, which may be constructed but cutting slots 144 in a tubular member and providing an undulation or indentation 143 in the resultant arm of material. The shaft extension and adaptor materials may be similar to those described in relation to FIG. 28 above.

FIG. 30 illustrates the distal portion of shaft extension 150, to which is attached adaptor 152. The distal end 151 of the shaft extension 150 is stepped down in diameter to fit within the lumen of adaptor 152 to which it is attached. This attachment may comprise a weld, a bond, an interference fit or other suitable attachment means. The adaptor 152 comprises a braided structure comprising a plurality of wire elements 153. This structure is intended to function in a similar fashion to that of a Chinese finger trap—in other words when placed in tension it will grip the proximal end of a clot retrieval shaft such as part 121 of shaft 120 shown in FIG. 27, provided the part 121 has a slightly larger outer diameter than the inner diameter of the braided adaptor 152.

FIGS. 31*a* to 31*d* illustrate a clot retrieval device 200 of this invention comprising an extendable shaft. The clot retrieval device 200 comprises a clot engaging portion 201 attached to the distal end of shaft 202. Shaft 202 further comprises a distal region 211, a proximal region 203, and an extension member 205. Extension member 205 fits within the lumen of the tubular proximal region 203, so that it does not interfere with device use in any way unless it is necessary for the shaft to be extended. This necessity might arise in a situation where it was desirable to remove the microcatheter through which the clot retrieval device had been delivered for example, or in a situation where it was desirable to advance a catheter over the shaft of the clot retrieval device which had not been placed in position prior to clot retrieval device delivery.

Shaft 202 may be constructed from a tubular element such as a Nitinol or other metal hypotube, and profiled and/or slotted at points along its length to tailor its flexibility. In another embodiment the proximal region of shaft 202 comprises a hypotube while the distal region 211 comprises a tapered wire element.

Figure 31A:
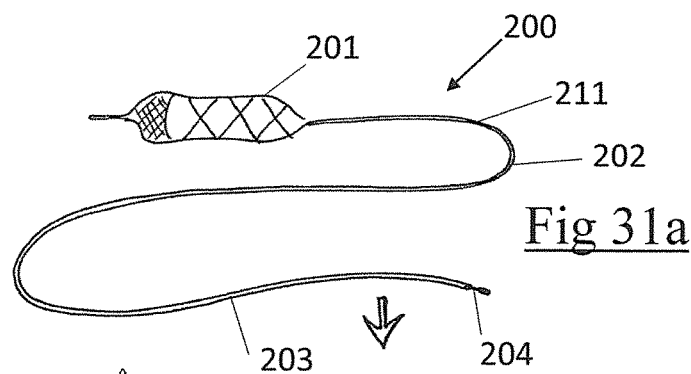
FIGS. 31a to 31d are views of a clot retrieval device with an extendable shaft.
Figure 31B:
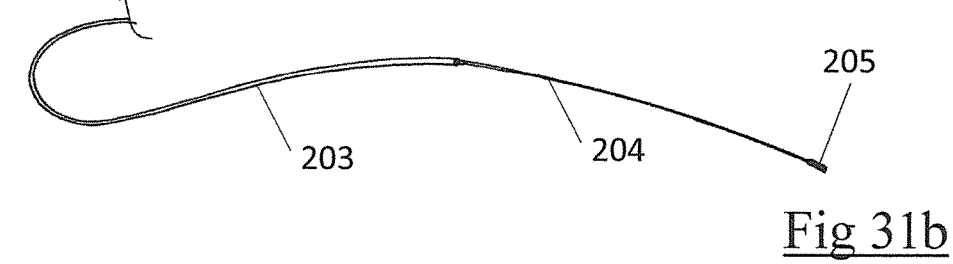

FIG. 31*a* shows the clot retrieval device 200 with the extendable shaft 204 in the non-extended position. FIG. 31*b* shows the proximal portion 203 of the shaft 202 of the clot retrieval device 200 with the extension member 204 in the extended position.

Figure 31C:
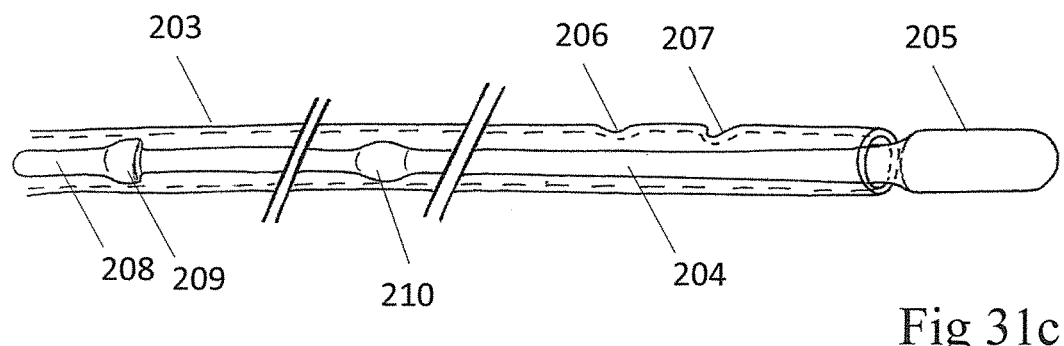

FIG. 31*c* shows a detailed partially sectioned view of the proximal portion 203 of the shaft 202 of the clot retrieval device 200 with the extension member 204 in the non-extended position. The extension member 204 comprises a proximal end 205 and a distal end 208. The outer diameter of the main body of the extension member is sized to be at least 0.001" and ideally 0.002" or more smaller than the inner diameter of the proximal shaft 203. The extension member 204 further comprises raised profiles 209 and 210 which are intended to interfere with indentations 206 and 207 in the proximal shaft 203. This enables the extension member 204 to be extended to an intermediate length whereby the raised profile 210 is positioned between indentations 206 and 207. The profile 210 and the indentations 206 and 207 are configured such that the user can pull the profile 210 past indentation 206 with a moderate amount of force, with this force being greater than that which would be applied to the shaft or extension member during advancement or retraction of a catheter over the shaft or extension member. This intermediate position allows the user to create the scenario described in relation to FIG. 7, where the shaft length is now sufficiently long to allow the user to safely retract a microcatheter through the tortuous distal region of the anatomy before he/she loses control of the shaft, but not so long as to provide a hindrance to the procedure, which could add to procedural time and patient risk.

The profile 209 is configured such that the user can pull the profile 209 past indentation 206 with a moderate amount of force, but not past indentation 207, which acts as a limit stop preventing complete removal of the extension member from the shaft. This fully extended position allows the user access to a full length shaft extension sufficient to enable him/her to advance a new catheter over the shaft and up to the clot engaging portion of the device without losing control of the device shaft while doing so.

Figure 31D:
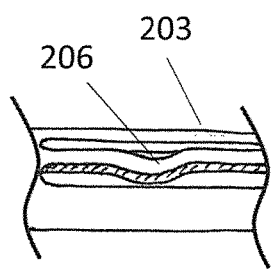

FIG. 31*d* shows a detail view of the distal indentation 206 of the proximal region 203 of the shaft 202. This indentation may be formed in a similar manner to that described in relation to FIG. 29 above.

Figure 32A:
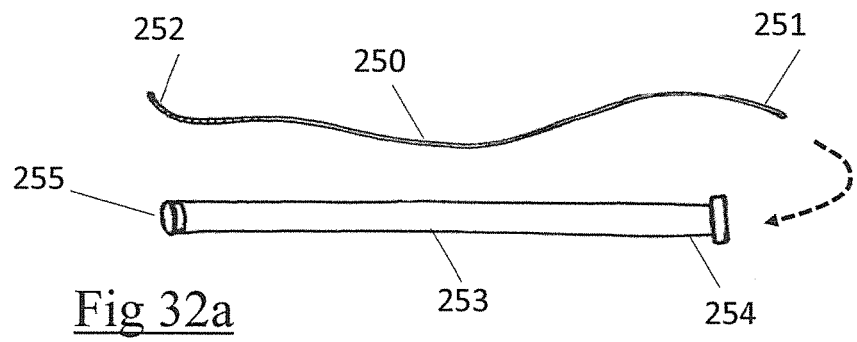
FIGS. 32a to 32d are views of a method of use of a system of the invention.

FIGS. 32*a* to 32*d* illustrate a method of use of a system of this invention to advance a catheter 253 over the shaft of a clot retrieval device 257 after the clot retrieval device has been deployed and the microcatheter through which it was initially delivered has been removed. The method involves the use of a standard guidewire 250, such as the guidewire that might have been used to deliver the microcatheter to the site of the occlusive clot in the first place. Use of a guidewire for this purpose is also described in relation to FIGS. 16 and 17, and adaptors 260 at the proximal end of the clot retrieval device shaft 259 to permit attachment of a standard guidewire as an extension member are also described previously herein. However a difficulty that can be encountered when using this method is that it can be difficult to introduce a catheter 253 over the floppy distal of a guidewire, as the tip can prolapse and/or snag within the catheter. To solve this problem the guidewire can first be loaded into the catheter by passing the firm proximal end 251 of the guidewire into the proximal end 254 of the catheter, and advancing the guidewire fully through the catheter until the proximal end of the guidewire exits the distal tip 255 of the catheter, as shown in FIG. 32*a*.

Figures 32B, 32C, 32D:
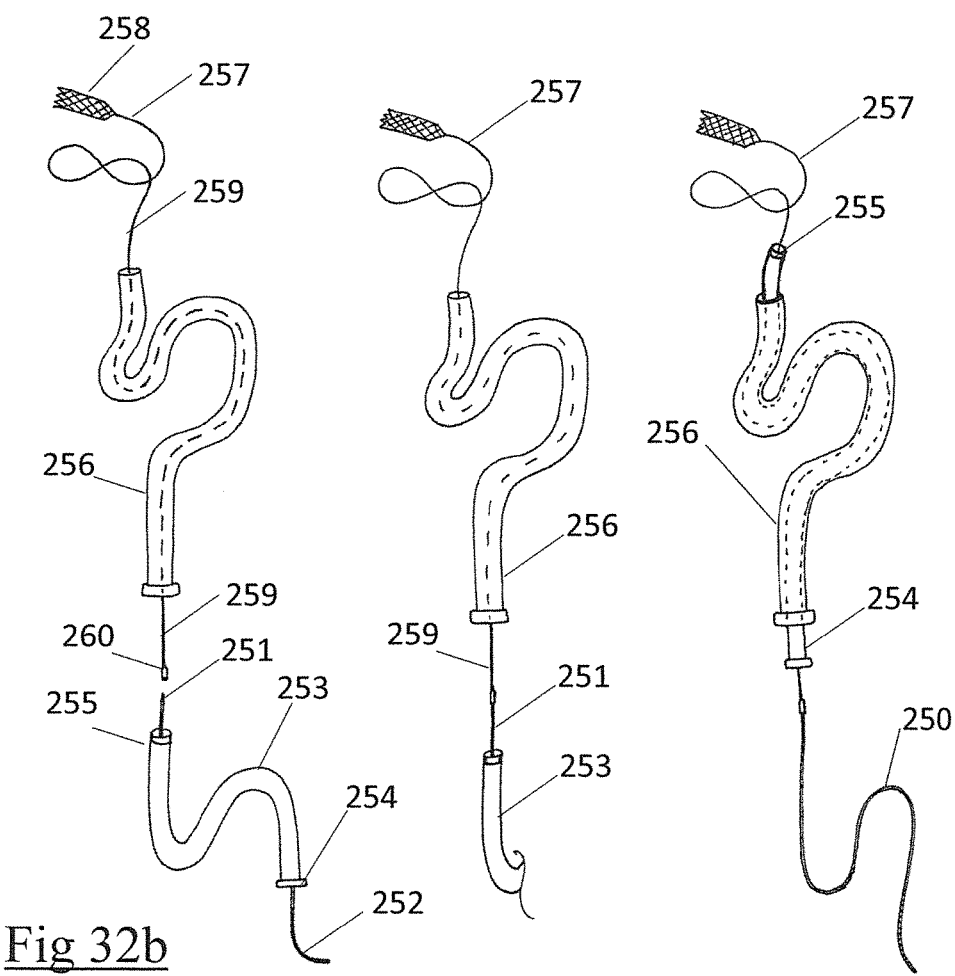

FIGS. 32*b* to 32*d* show the next steps of this method, namely: connecting the proximal end 251 of the guidewire to the adaptor 260 on the proximal end of the clot retrieval device shaft, advancing the catheter 253 over the guidewire and on over the clot retrieval device shaft 259 and into the guide catheter or sheath 256, while retaining control of the distal end of the guidewire 252; continuing to advance the catheter 253 over the guidewire and the clot retrieval device shaft until the catheter exits the guide/sheath and reaches the target location, at which point the adaptor should have exited the proximal end of the catheter as shown in FIG. 32*d*.

The invention may be utilised in conjunction with any suitable clot retrieval devices such as those described in our WO2012/120490A. In some cases the clot retrieval device comprises an inner elongate body and an outer elongate body which are radially spaced-apart to define a clot receiving space therebetween. The outer elongate body may have large clot receiving openings which are substantially larger than openings in the inner elongate body. Because the device is configured with a long inner expandable member, this member can extend proximal of even a very long clot and upon device deployment the expansion of this member creates a flow channel through the clot, restoring flow to the vascular bed distal of the clot and reducing the pressure gradient across the clot. This reduction in pressure gradient reduces the force required to disengage the clot from the vessel wall and retract it proximally. The scaffolding regions of the outer expandable member expand within the distal portion of the clot applying a compressive force to discrete regions of the clot, thus urging the clot to flow away from these regions, through the inlet openings and into the reception space between the inner and outer members. This causes compression in discrete regions of the clot, but causes minimal compression in regions of the clot, or in the region proximal of the outer member. Minimizing compression on the clot in this way minimizes the forces applied radially outward to the vessel wall, which in turn reduces the frictional force to be overcome when retracting the clot.

Because the inner member has created a channel through which blood can pass to the distal vascular bed, the device can be safely left in place for a dwell period prior to withdrawal. This dwell period is desirably greater than one minute and may be as long as 30 minutes or more. Allowing the device to sit in this way allows the clot to flow into the device which facilitates gripping it securely for retrieval. It also allows the distal vascular bed to be gently perfused with fresh oxygenated blood rather than be exposed to a sudden jump in pressure and flow as would be the case if the clot were immediately removed or if the device were to compress the clot so much that a very large flow channel was created upon deployment. Once the dwell period has elapsed the device and microcatheter can be retracted back into either the DAC or guide/sheath. This may be done with the aid of aspiration through the guide/sheath or DAC to assist in retaining a firm grip on the clot and avoiding fragment loss, however the disclosed designs which grip the clot securely and house the clot safely within a reception space and further comprise a distal net or scaffolding region have the advantage that they can be safely used without aspiration. The distal net may be spaced apart from the distal end of the outer member as shown such that it is optimally positioned to trap any fragments released from the clot during retraction even if these fragments originate from that portion of the clot not fully housed with reception space.

It will be apparent from the foregoing description that, while particular embodiments of the present invention have been illustrated and described, various modifications can be made without departing from the spirit and scope of the invention. Accordingly, it is not intended that the present invention be limited and should be defined only in accordance with the appended claims and their equivalents.

The invention claimed is:

1. A method for retrieving a clot from a vasculature comprising:
   providing a first catheter;
   providing a second catheter over the first catheter;
   providing a clot retrieval device having a compressed delivery configuration in the first catheter and an expanded deployed configuration distal of the first catheter, the clot retrieval device having a shaft;
   deploying the clot retrieval device from the first catheter;
   extending a length of the shaft from a proximal end of the shaft, the proximal end of the shaft being proximal of the first and second catheters; and
   retracting and removing the first catheter over the shaft whilst maintaining control of the proximal end of the shaft.

2. The method as claimed in claim 1 further comprising applying aspiration to the clot through a lumen of the second catheter after retraction of the first catheter over the retrieval device shaft.

3. The method as claimed in claim 2 wherein the first catheter is a delivery catheter for the clot retrieval device and the method further comprises deploying the clot retrieval device from the delivery catheter and subsequently retracting the delivery catheter over the clot retrieval device shaft.

4. The method as claimed in claim 3 further comprising delivering the second catheter over the extended length of the shaft and distally towards the clot.

5. The method as claimed in claim 1 wherein the extending the length includes connecting one end of an adaptor to the proximal end of the device shaft and connecting a proximal shaft extension to another end of the adaptor.

6. The method as claimed in claim 1 wherein the shaft comprises an extension member and the method further comprises moving the extension member from a retracted to an extended configuration prior to retraction of the first catheter.

7. The method as claimed in claim 1 wherein the extending the length includes extending the length to between 2.1 and 2.3 meters.

8. A method for retrieving a clot from a vasculature, comprising:
   advancing a first catheter to a target location distal of an aortic arch of a patient, at least a portion of the first catheter translatably disposed within a lumen of a second catheter;
   deploying a clot retrieval device, the clot retrieval device being expandable between a delivery configuration within the first catheter and a deployed configuration distal of the first catheter and being coupled to a distal end of a shaft at least partially disposed within a lumen of the first catheter;
   extending a length of the shaft from a proximal end of the shaft, the proximal end of the shaft being proximal of the first and second catheters; and
   retracting the first catheter relative to the second catheter and proximal of the aortic arch while maintaining control of the clot retrieval device via the proximal end of the shaft.

9. The method as claimed in claim 8 further comprising applying aspiration through the lumen of the second catheter after the retracting the first catheter.

10. The method as claimed in claim 8 wherein extending the length includes connecting a first end of an adaptor to the proximal end of the shaft and connecting a proximal shaft extension to a second end of the adaptor.

11. The method as claimed in claim 8 wherein the shaft comprises an extension member and the method further comprises moving the extension member from a retracted configuration to an extended configuration prior to the retracting the first catheter.

12. The method as claimed in claim 8 wherein an extended length of the shaft is between 2.1 and 2.3 m.

13. The method as claimed in claim 8 further comprising retracting the second catheter into a lumen of a third catheter.

14. A method for retrieving a clot from a vasculature, comprising:
   advancing a first catheter to a target location, at least a portion of the first catheter disposed within a lumen of a second catheter;
   deploying a clot retrieval device, the clot retrieval device being expandable between a delivery configuration within the first catheter and a deployed configuration distal of the first catheter and being coupled to a distal end of a shaft at least partially disposed within the first catheter;
   extending a length of the shaft from a proximal end of the shaft, the proximal end of the shaft being proximal of the first and second catheters;
   retracting the first catheter relative to the second catheter while maintaining control of the clot retrieval device via the proximal end of the shaft; and
   applying aspiration through the lumen of the second catheter.

15. The method as claimed in claim 14 wherein the extending the length includes connecting a first end of an adaptor to the proximal end of the shaft and connecting a proximal shaft extension to a second end of the adaptor.

16. The method as claimed in claim 14 wherein the shaft comprises an extension member and the method further comprises moving the extension member from a retracted configuration to an extended configuration prior to the retracting the first catheter.

17. The method as claimed in claim 14 wherein an extended length of the shaft is between 2.1 and 2.3 m.

18. The method as claimed in claim 14 further comprising retracting the second catheter into a lumen of a third catheter.

19. The method as claimed in claim 14 wherein the applying aspiration is performed after the retracting the first catheter.

* * * * *